United States Patent [19]

Chown et al.

[11] 3,980,767

[45] Sept. 14, 1976

[54] GEL TOOTHPASTES

[75] Inventors: James Philip Chown, Stokes Poges; John Maxwell Healey, Byfleet, both of England

[73] Assignee: Beecham Group Limited, Great Britain

[22] Filed: Oct. 15, 1974

[21] Appl. No.: 514,376

Related U.S. Application Data

[63] Continuation of Ser. No. 299,540, Oct. 20, 1974, abandoned, which is a continuation of Ser. No. 149,783, June 3, 1971, abandoned, which is a continuation-in-part of Ser. No. 843,621, July 22, 1969, abandoned.

[30] Foreign Application Priority Data

July 23, 1968 United Kingdom............... 35109/68

[52] U.S. Cl.................................... 424/52; 424/49
[51] Int. Cl.².......................................... A61K 7/18

[58] Field of Search................................. 424/52, 49

[56] References Cited
UNITED STATES PATENTS 3,574,823  4/1971  Roberts et al. ...................... 424/49

*Primary Examiner*—Joseph Paul Brust
*Assistant Examiner*—Cary Owens

[57] ABSTRACT

The invention relates to a toothpaste having a main body which is a transparent or translucent gel and secondary body of cleaning and polishing toothpaste contained within the main body in the form of a core or cores or stripe or stripes. The secondary body may contain materials, such as compounds of calcium or other polyvalent metals, which are normally incompatible with the transparent or translucent gel state of the main body.

7 Claims, 1 Drawing Figure

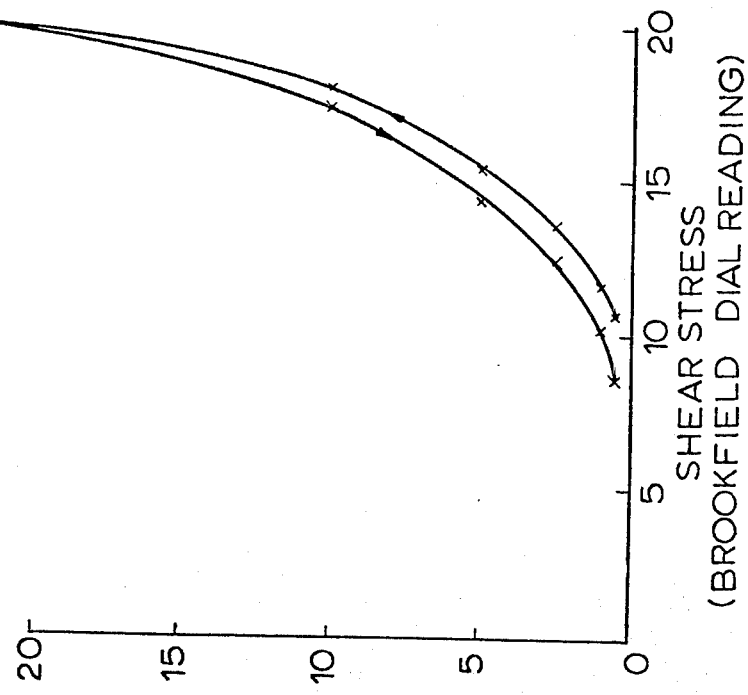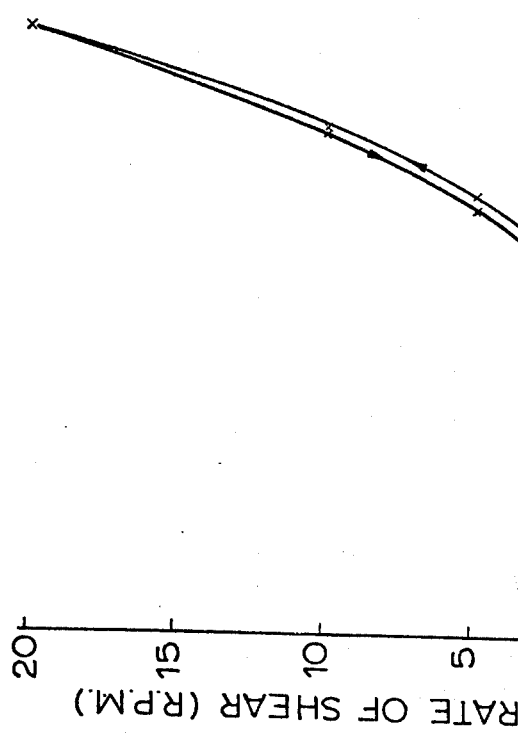

GEL TOOTHPASTES

REFERENCE TO RELATED APPLICATION

The present application is a continuation of application Ser. No. 299,540 filed Oct. 20, 1974 and now abandoned which is a continuation of Ser. No. 149,783 filed June 3, 1971 and now abandoned which is a continuation-in-part of copending patent application Ser. No. 834,621 filed July 22, 1969 and now abandoned.

BACKGROUND OF THE INVENTION

Transparent toothpastes are commercially attractive, but suffer from the disadvantage that they do not usually have satisfactory tooth cleaning or tooth polishing properties. Accordingly, an object of the present invention is to overcome this disadvantage.

BRIEF SUMMARY OF THE INVENTION

The present invention provides a portion of toothpaste comprising a main body of toothpaste which is a transparent or translucent gel and a secondary body of cleaning and polishing toothpaste contained within the main body. The secondary body may be completely contained within the gel to provide a core or cores surrounded by the main body of toothpaste or it may be in the form of a stripe or stripes only partly contained within the main body so that a portion of the surface of the stripe or stripes is exposed at the surface of the main or gel body of the toothpaste.

It has been discovered that substances which are normally incompatible with the main body, in that they would strongly adversely affect or destroy the light transmitting gel state of the main body if admixed therewith even in small quantities, may be included in the secondary body even as a major component without significantly or observably affecting the stability of the light transmitting gel state of the main body. For example, compounds of the polyvalent metals, such as chalk, dicalcium phosphate dihydrate and calcium pyrophosphate which are highly useful as dental abrasives, as well as other well known substances which are incompatible with the main body in the above sense, may be included in the secondary body without affecting the stability of the main body. This result is highly unexpected and useful.

The invention also provides a collapsible tube or other container containing a main body of toothpaste which is a transparent or translucent gel and a secondary body or bodies which is, or each of which is, of cleaning and polishing toothpaste material, the secondary body or bodies being so arranged within the tube or container that when the tube or container is collapsed to discharge a portion of toothpaste the secondary body or bodies will be discharged as a stripe or stripes or core or cores within the main body. The tube is preferably charged with the main and secondary bodies of toothpaste by the method and filling nozzle described in British Patent Specification No. 962,757.

BRIEF DESCRIPTION OF THE ACCOMPANYING DRAWINGS

The drawings are Brookfield Rheograms of a toothpaste according to the invention.

DESCRIPTION OF A PREFERRED EMBODIMENT

In a preferred embodiment of the invention, the main body or toothpaste material is gel containing water and humectant such as glycerin, sorbitol, propylene glycol or a polyethylene glycol, together with a detergent, sweetening agent, flavour, preservative and other ingredients necessary to obtain an acceptable product. It may also contain a therapeutic material. Suitable flavours include peppermint, spearmint and aniseed oils and mixtures thereof. Suitable sweetening agents include sodium cyclamate and saccharin.

The main body of mixture may be thickened with a suitable gum or thickening agent of either natural, cellulosic or synthetic origin. Other possible thickening agents are carageenates, alginates, and cellulose ethers and esters.

The main body may be thickened with inorganic materials such as colloidal silica, providing that the refractive indices of the thickening agent and the gel are approximately the same.

The main body may be coloured if desired, provided it remains reasonably transparent or translucent.

The consistency of the main body needs to be firm enough to hold the secondary body in position and yet be easily extrudable through the nozzle of a toothpaste tube.

A secondary body or bodies of cleaning and polishing toothpaste material is, or are, contained within the main body so that when toothpaste is discharged from a tube it, or they, will be either completely enclosed as a core or cores or partly enclosed as a stripe or stripes.

The cleaning and polishing effect on teeth is controllable within wide limits by the composition of the secondary body or bodies, and by the proportion of the stripe secondary material. For aesthetic reasons, it is preferable to keep the proportion of secondary material below 25% v/v. The secondary material includes a non-abrasive part which is of a composition such as to minimize diffusion or other undesirable action between the main and secondary bodies, which preferably have matched pH values.

The secondary material contains an abrasive which requires careful choice in order to obtain the correct level of cleaning and polishing, and to help maintain the correct rheological properties.

The secondary material also contains materials such as humectants, thickening agents and detergents to stabilize the phase and give the desired relogical properties. A suitable detergent is sodium laurylsulphate. For the optimum conditions, the rheological properties of the main and secondary bodies should be matched as closely as possible.

The abrasive can be any of the conventional toothpaste materials, such as chalk, dicalcium phosphate dihydrate, calcium, pyrophosphate or alumina or other less common inorganic materials, or polymeric materials such as polyvinyl chloride powder or polymethyl metharcrylate or blends of such materials. Choice of abrasive will depend to some extent upon the properties of the main body as the two bodies must be compatible over an extended period. It may also contain a therapeutic material.

The concentration of abrasive in the stripe or stripes or in the core or cores should be high and is preferably in the range of 15% to 75%. The abrasive must be fairly coarse and yet acceptable for the dental enamel, dentine and cementium. The proportion of abrasive used in normally less than that of conventional toothpastes, but should be as high as possible consistent with maintaining the rheological properties of the secondary body similar to those of the main body.

The secondary material may be coloured if required for example by an insoluble colouring material.

In a typical toothpaste according to the invention, the proportions of the main and secondary bodies would be 99.8% to 90% main body and 0.2% to 10% secondary body. These would be 15% to 75% abrasive in the secondary body. The toothpaste may contain 10% to 80% humectants, 0 to 2% sweetening agent, 0.1% to 2.5% flavouring, and 0.25% to 5% detergent.

EXAMPLE 1

| Main Body of Toothpaste | %w/w |
|---|---|
| Carboxyvinyl polymer ("Carbopol" 940) | 1.25 |
| 70% sorbitol solution | 15.00 |
| Glycerin | 15.00 |
| Water | 67.15 |
| Sweetening Agent (Saccharin) | 0.10 |
| Flavour (Peppermint oil) | 0.50 |
| Detergent (Sodium Laurylsulphate) | 1.00 |
| | 100.00 |
| Secondary Body or Bodies of Toothpaste | |
| Carboxyvinyl polymer ("Carbopol" 940) | 0.51 |
| 70% Sorbitol solution | 7.18 |
| Glycerin | 7.18 |
| Water | 32.69 |
| Sweetening Agent (Saccharin) | 0.05 |
| Flavour (Peppermint oil) | 0.24 |
| Detergent (Sodium Laurylsulphate) | 0.47 |
| Abrasive (Chalk) | 52.5 |
| | 100.00 |

The secondary material to main body is 12:100.

"Carbopol" is a trade mark of Union Carbide Corporation.

In Example 1, the "Carbopol" was neutralized to pH7-9 with a base such as sodium hydroxide, triethanolamine so that it can act as thickening agent.

The rheological properties of the product of Example 1, are shown in the rheograms which form the accompanying drawings. These diagrams illustrate that the gel and secondary body behave quite similarly when undergoing various shearing stresses. The secondary body is marginally more viscous and slightly thixotropic when compared to the gel, but these differences are small. The measurements were taken with a Brookfield Viscometer (Model RVT) and a Spindle TD immersed to a depth of 4 cms. The spindle was rotated at the lowest speed for two minutes, and the dial reading was noted. A reading was then taken after one minutes at each successive increase in speed of rotation of the spindle up to a maximum speed of 20 rpm. This was repeated as the speed of rotation was reduced step-wise down to 0.5 rpm. Measurements were taken at 0.5, 1.0, 2.5, 5.0, 10.0 and 20.0 r.p.m.

The product of Example I, even though the secondary body contains chalk as a major component, was completely stable even after storage at room temperature for a year. No deterioration of the transparent gel state of the main body was observed after this storage period.

EXAMPLE 2

| Main Body of Toothpaste | % w/w |
|---|---|
| Carboxyvinyl polymer ("Carbopol" 934) | 1.5 |
| Propylene Glycol | 30.0 |
| Water | 65.4 |
| Sweetening agent (Saccharin) | 0.10 |
| Flavour (Peppermint oil) | 1.0 |
| Detergent (Sodium Laurylsulphate) | 2.0 |
| | 100.00 |

| Secondary Body or Bodies of Toothpaste | |
|---|---|
| Carboxyvinyl polymer ("Carbopol" 934) | 0.65 |
| Propylene Glycol | 14.36 |
| Water | 31.54 |
| Sweetening agent (Saccharin) | 0.05 |
| Flavour (Peppermint oil) | 0.5 |
| Detergent (Sodium Laurylsulphate) | 0.9 |
| Abrasive (Dicalcium phosphate dihydrate) | 50.0 |
| | 100.0 |

The ratio of secondary material to main body material is 12:100 by weight.

In this Example, the "Carbopol" was neutralized as in Example 1.

Like the product of Example 1, the product of Example 2 was highly stable.

EXAMPLE 3

| Main Body of Toothpaste | % w/w |
|---|---|
| Carboxyvinyl polymer ("Carbopol" 940) | 1 |
| Carboxymethylcellulose | 1 |
| 70% Sorbitol Solution | 10 |
| Glycerine | 15 |
| Propylene Glycol | 15 |
| Water | 53.7 |
| Sweetening agent (sodium cyclamate) | 0.5 |
| Flavour (Peppermint - aniseed oils) | 1 |
| Detergent (sodium laurylsulphate and sodium decylsulphate in ratio 3:1) | 2 |
| Sodium Monofluorophosphate | 0.8 |
| | 100.0 |
| Secondary Body or Bodies of Toothpaste | |
| Carboxyvinyl polymer ("Carbopol" 940) | 0.6 |
| Carboxymethylcellulose | 0.5 |
| 70% Sorbitol solution | 4.72 |
| Glycerine | 5.72 |
| Propylene glycol | 6 |
| Water | 25.41 |
| Sweetening agent (sodium cyclamate) | 0.25 |
| Detergent (sodium laurylsulphate and sodium decylsulphate in ration 3:1) | 0.9 |
| Sodium monofluorophosphate | 0.4 |
| Polymethyl methacrylate abrasive | 55 |
| | 100.00 |

The ratio of secondary material to main material is 20:100 by weight. This is an anticaries toothpaste.

In this Example the "Carbopol" is Neutralized as in Example 1.

EXAMPLE 4

| Main Body of Toothpaste | % w/w |
|---|---|
| Colloidal silica | 5.0 |
| Carboxyvinyl polymer ("Carbopol" 940) | 0.5 |
| Glycerine | 75.0 |
| Water | 17.9 |
| Sweetening agent (Saccharin) | 0.1 |
| Flavour (Spearmint oil) | 0.5 |
| Detergent (sodium laurylsulphate) | 1.0 |
| | 100.0 |
| Secondary Body or Bodies of Toothpaste | |
| Colloidal silica | 2.0 |
| Carboxyvinyl polymer ("Carbopol" 940) | 0.3 |
| Glycerine | 45.0 |
| Water | 10.9 |
| Sweetening agent (Saccharin) | 0.05 |
| Flavour (Spearmint oil) | 0.24 |
| Detergent (sodium laurylsulphate) | 0.47 |
| Abrasive (calcium pyrophosphate) | 40.0 |
| | 100.00 |

The ratio of secondary material to main body material is 15:100 by weight.

As in the earlier Examples, the product of Example 4 is highly stable even after long storage periods.

We claim:

1. A toothpaste consisting essentially of a first transparent gel body substantially free of dental abrasive and a second gel body or bodies comprising a solid finely divided dentally acceptable abrasive, said second gel body or bodies being partially or wholly disposed within the first gel body, the first gel body and second gel body or bodies having similar rheological properties.

2. A toothpaste according to claim 1 wherein the second gel body or bodies comprising the abrasive is or are disposed as an optically contrasting stripe or stripes extending longitudinally of said first gel body.

3. A toothpaste according to claim 1 wherein the second gel body or bodies comprising the abrasive is or are disposed as an optically contrasting core or cores wholly within the first gel body.

4. A toothpaste according to claim 1 wherein the first gel body and the second gel body or bodies have substantially the same composition except for the abrasive.

5. A toothpaste according to claim 1 wherein the abrasive constitutes 15 to 75% by weight of the second gel body or bodies.

6. A toothpaste according to claim 1 wherein the first gel body constitutes about 99.8 to 90% by weight of the toothpaste and the second gel body constitutes about 0.2 to 10% by weight thereof.

7. A toothpaste according to claim 1 wherein each gel body contains an effective amount of sodium monofluorophosphate less than 1%.

* * * * *